United States Patent
Bao et al.

(10) Patent No.: US 8,562,593 B2
(45) Date of Patent: Oct. 22, 2013

(54) VARIABLE CRYOSURGICAL PROBE PLANNING SYSTEM

(75) Inventors: Shenghao Bao, Ladera Ranch, CA (US); Jay J. Eum, Irvine, CA (US)

(73) Assignee: Endocare, Inc., Austin, TX (US)

( * ) Notice: Subject to any disclaimer, the term of this patent is extended or adjusted under 35 U.S.C. 154(b) by 0 days.

(21) Appl. No.: 13/481,557

(22) Filed: May 25, 2012

(65) Prior Publication Data
US 2012/0239018 A1 Sep. 20, 2012

Related U.S. Application Data

(63) Continuation of application No. 11/618,492, filed on Dec. 29, 2006, now Pat. No. 8,187,260.

(51) Int. Cl.
*A61B 17/00* (2006.01)

(52) U.S. Cl.
USPC .................................................. 606/1; 700/83

(58) Field of Classification Search
USPC ......... 606/1, 20–26; 700/17, 83, 87; 702/155, 702/158, 166–169; 361/679.21, 679.22; 33/713, 720; 128/898
See application file for complete search history.

(56) References Cited

U.S. PATENT DOCUMENTS

| | | | |
|---|---|---|---|
| 4,672,963 A | 6/1987 | Barken | |
| 5,531,742 A | 7/1996 | Barken | |
| 5,706,810 A | 1/1998 | Rubinsky et al. | |
| 5,800,487 A | 9/1998 | Mikus et al. | |
| 6,074,412 A | 6/2000 | Mikus et al. | |
| 6,139,544 A | 10/2000 | Mikus et al. | |
| 6,142,991 A | 11/2000 | Schatzberger | |
| 6,206,832 B1 | 3/2001 | Downey | |
| 6,423,009 B1 | 7/2002 | Downey | |
| 6,512,942 B1 | 1/2003 | Burdette et al. | |
| 6,610,013 B1 | 8/2003 | Fenster et al. | |
| 6,643,535 B2 | 11/2003 | Damasco et al. | |
| 6,694,170 B1 | 2/2004 | Mikus et al. | |
| 6,905,492 B2 | 6/2005 | Zvuloni | |
| 7,909,227 B2 | 3/2011 | Duong et al. | |
| 8,094,894 B2 | 1/2012 | Nagler et al. | |
| 2004/0044295 A1* | 3/2004 | Reinert et al. | 600/587 |
| 2004/0267248 A1 | 12/2004 | Duong et al. | |
| 2005/0010200 A1 | 1/2005 | Damasco et al. | |
| 2005/0192565 A1 | 9/2005 | Eum et al. | |
| 2007/0038223 A1* | 2/2007 | Marquart et al. | 606/86 |

\* cited by examiner

*Primary Examiner* — Ahmed Farah
(74) *Attorney, Agent, or Firm* — Lawrence N. Ginsberg

(57) ABSTRACT

A cryosurgical system for assisting an operator in placing and operating cryosurgical probes in the prostate of a human patient. The cryosurgical system includes a computer system being programmed with software capable of performing the following steps: a) capturing a plurality of transverse views of the prostate; b) capturing a sagittal view of the prostate; c) outlining the capsule of the prostate, the urethra and the rectal wall of the patient with the assistance of the operator, utilizing the captured plurality of transverse views and the captured sagittal view; d) constructing a 3-dimensional model of the prostate, the urethra and the rectal wall utilizing the outlines of step c), above; and, e) utilizing the 3-dimensional model of the prostate, the urethra and the rectal wall to determine i) the number of cryosurgical probes to be utilized; ii) probe settings; and, iii) probe placement positions. The resultant ice thus produced by the cryosurgical probes is optimized for a specific patient.

15 Claims, 10 Drawing Sheets

SAGITTAL VIEW

TOP VIEW

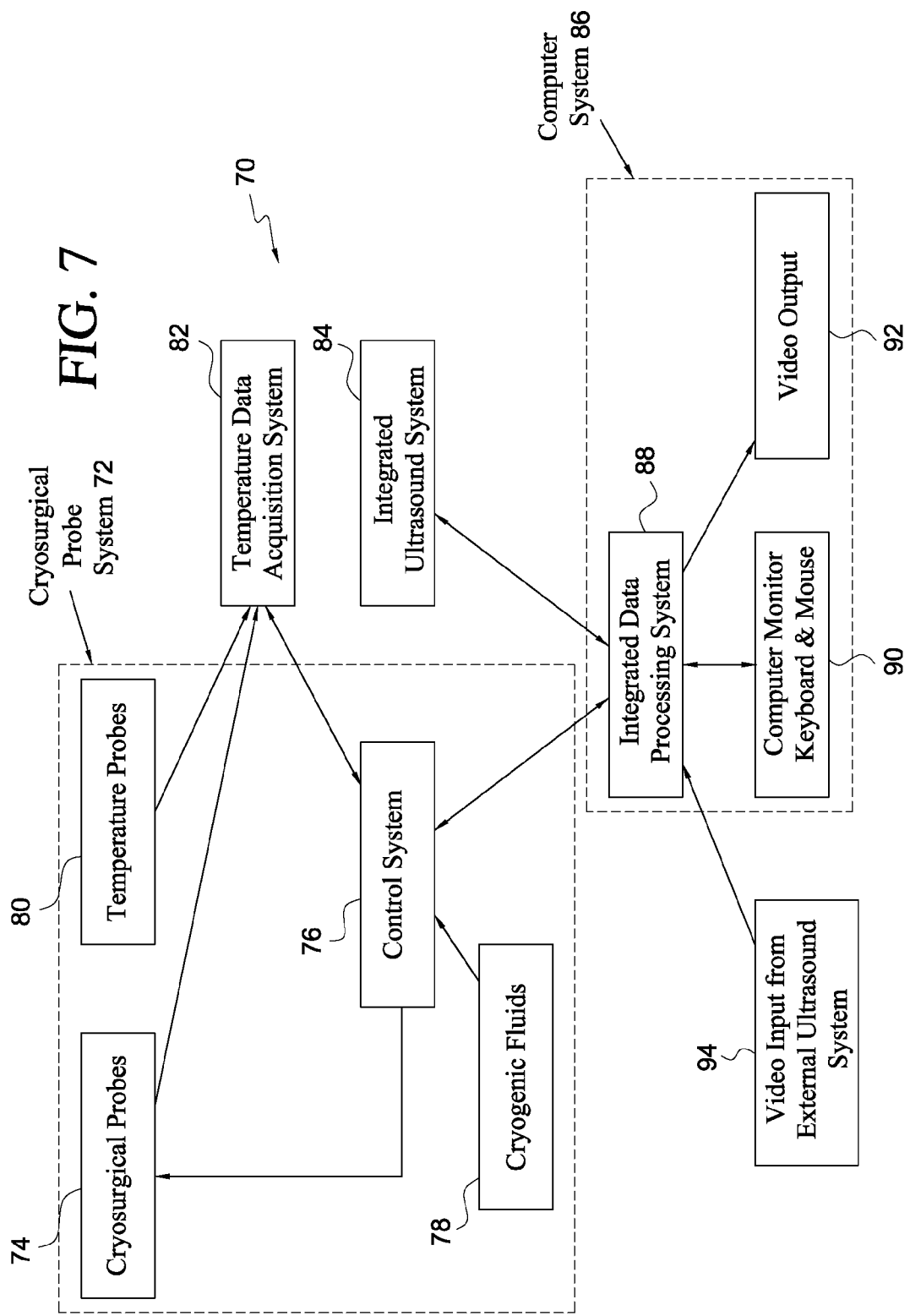

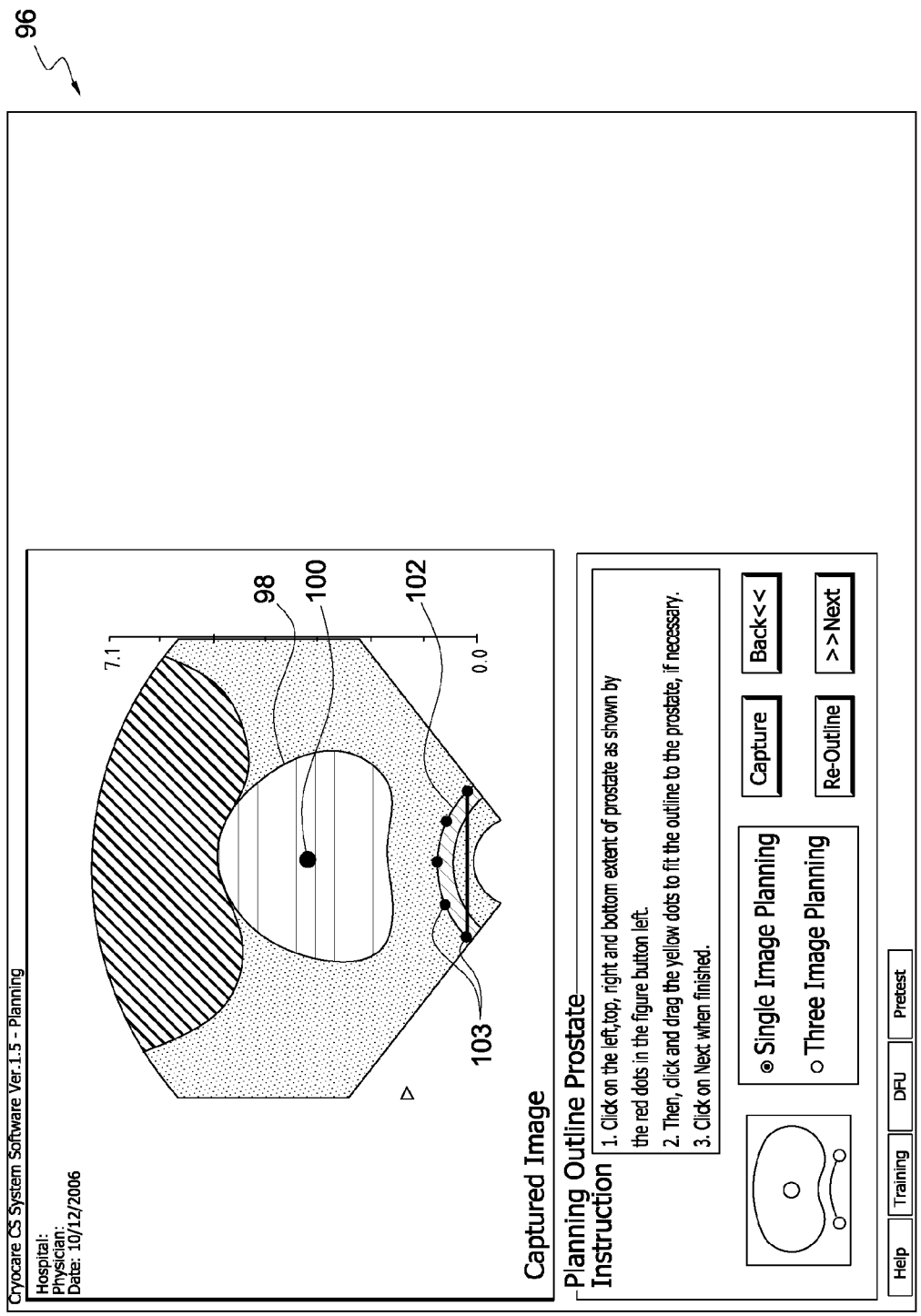

FIG. 9

Step 1 - TempProbe Placement

| Order | TempProbe | Grid | Temp(°C) |
|---|---|---|---|
| First | ANT / C | f 6.0 | 25.0 |
| Second | ES / F | f 3.0 | 24.0 |
| Third | DEN / A | f 1.5 | OPEN |
| Fourth | LNVB / D | h 2.0 | 24.0 |
| Fifth* | RNVB / B | D 2.0 | 23.0 |
| Sixth** | APEX / E | f 2.5 | 24.0 |

Note: * See step 3 for placing ES.
** APEX is optional.

Step 2 - CryoProbe Placement

| Order | CryoProbe | Grid | V-Ice | Medium ▼ |
|---|---|---|---|---|
| | | | | Long / Medium / Short |
| First | Probe 1 | E 5.0 | M | ON |
| Second | Probe 2 | H 5.0 | M | OFF |
| Third | Probe 3 | D 3.0 | L | OFF |
| Fourth | Probe 4 | h 3.0 | L | OFF |
| Fifth | Probe 5 | e 2.5 | S | OFF |
| Sixth | Probe 6 | G 2.5 | S | OFF |
| Seventh | Probe 7 | N/A | N/A | OFF |
| Eighth | Probe 8 | N/A | N/A | OFF |

Note: * Depth guidance is for sagittal view only

Step 3 - Cystoscope & Warmer Placement

| Order | Operations |
|---|---|
| First | Perform cystoscope to ensure no TempProbes or CryoProbes are in the urethra |
| Second | Perform cystoscope to look for correct ES TempProbe placement |
| Third | Insert guidewire through cystoscope, then remove cystoscope |
| Fourth | Insert urethra warming catheter over guidewire |

Placement: CryoProbe/TempProbe
1. Place TempProbes according to step 1.
2. Place CryoProbes according to step 2.
3. Place warming catheter according to step 3.
4. When all probes are placed, click Next button.

Order: ● Post -> Ant  ○ Ant -> Post

☑ Graphics  [Back<<]  [>>Next]

Cryocare CS System Software Ver.2.8 - Placement
Hospital:
Patient:
Physician:
Date: 10/12/2006

LIVE

[Help] [Training] [User Manual] [Pretest] [Reassign Port] [Measure] [Patient Info]

VARIABLE CRYOSURGICAL PROBE PLANNING SYSTEM

CROSS REFERENCE TO RELATED APPLICATIONS

This is a continuation of U.S. application Ser. No. 11/618,492, entitled "Variable Cryosurgical Probe Planning System", filed on Dec. 29, 2006, issued May 29, 2012 as U.S. Pat. No. 8,187,260 the entire contents of the application are incorporated herein by reference for all purposes in its entirety.

BACKGROUND OF THE INVENTION

1. Field of the Invention

The present invention relates to computer guided cryosurgery and more particularly to a system that utilizes a computer program optimizing the generation of resultant ice produced for a specific patient.

2. Description of the Related Art

Cryosurgery involving the use of a cryosurgical probe assemblies typically involves the use of cryoprobes that are each attached to a handle that are, in turn, connected to a high-pressure fluid line attached to a fluid source. Cryosurgical ablation of the prostate has generally required relatively small iceballs, i.e. 4 cm diameter by 6 cm length. For other applications, for example, renal applications, relatively larger iceballs are desired. Many other potential applications of cryosurgery may also require larger iceballs such as to ablate renal tumors, hepatic tumors, and pulmonary and thoracic tumors. Relatively large iceballs may also be required for palliative intervention.

The ultimate goal in a cryosurgical procedure is to freeze all tumor tissue by lethal ice to kill tumor and not to freeze any benign tissue surround tumor tissue by lethal ice to avoid complications. Due to variations of tumor size and shape, it has always been a great challenge for a cryosurgeon to precisely place multiple cryosurgical probes into desired locations of a tumor and control them so as to generate an optimum lethal iceball that is tailored to fit the tumor.

SUMMARY OF THE INVENTION

In a broad aspect, the present invention is a cryosurgical system for assisting an operator in placing and operating cryosurgical probes in the prostate of a human patient. The cryosurgical system includes a computer system being programmed with software capable of performing the following steps:
  a) capturing a plurality of transverse views of the prostate;
  b) capturing a sagittal view of the prostate;
  c) outlining the capsule of the prostate, the urethra and the rectal wall of the patient with the assistance of the operator, utilizing the captured plurality of transverse views and the captured sagittal view;
  d) constructing a 3-dimensional model of the prostate, the urethra and the rectal wall utilizing the outlines of step c), above; and,
  e) utilizing the 3-dimensional model of the prostate, the urethra and the rectal wall to determine i) the number of cryosurgical probes to be utilized; ii) probe settings; and, iii) probe placement positions.

The resultant ice thus produced by the cryosurgical probes is optimized for a specific patient.

The cryosurgical system preferably includes an ultrasound system and graphical depth guide software capable of providing a graphical overlay on an ultrasound image for assisting in the placement of the cryosurgical probes.

Although the present inventive principles will be discussed in detail with respect to their application to the prostate they may have many additional applications. Some additional particular applications include ablation of renal tumors, hepatic tumors, and pulmonary and thoracic tumors. Relatively large iceballs may also be required for palliative intervention. Such additional applications involve the selection of regions of interest and subregions within these regions in order to provide the modeling.

BRIEF DESCRIPTION OF THE DRAWINGS

FIG. 7 is a block diagram of a preferred embodiment of the cryosurgical system of the present invention.

FIG. 8 is an example screen display showing a captured image of the outline of the middle gland of the prostate on the transverse view.

FIG. 9 is an example screen display showing the utilization of the depth guide of the present invention.

DETAILED DESCRIPTION OF THE INVENTION

Figure 1:
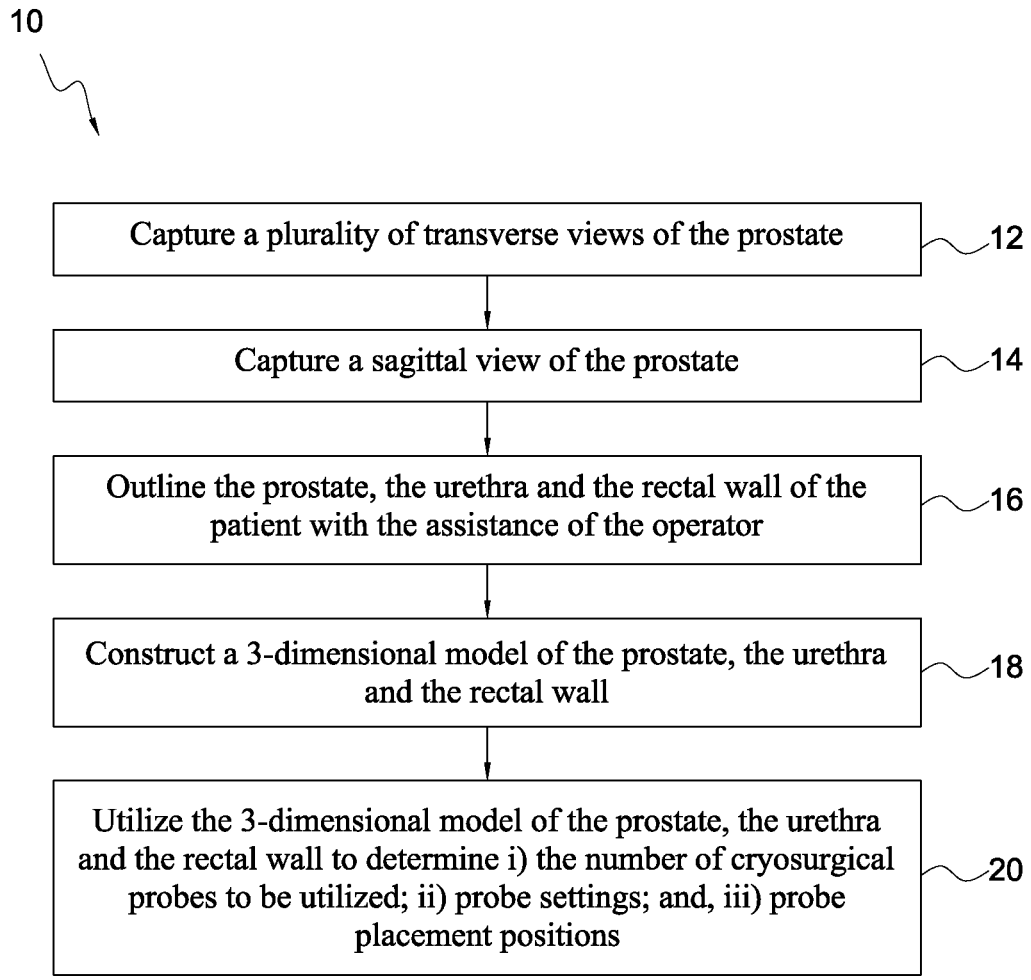
FIG. 1 is flow chart illustrating, in a broad aspect, the steps implemented by the software of the computer system of the cryosurgical system of the present invention.

Referring now to the drawings and the characters of reference marked thereon, FIG. 1 illustrates, in a broad aspect, the steps implemented by the computer system of the present invention to optimize usage of cryosurgical probes for a specific patient. These steps are designated generally as 10. In a first step, the computer system captures a plurality of transverse views of the prostate, as noted by numeral designation 12. It then captures a sagittal view of the prostate (process block 14). The capsule of the prostate, the urethra and the rectal wall of the patient are outlined with the assistance of the operator, utilizing the captured plurality of transverse views and the captured sagittal view (process block 16). A 3-dimensional model of the prostate, the urethra and the rectal wall is constructed utilizing the outlines noted above (process block 18). The 3-dimensional model is used to determine i) the number of cryosurgical probes to be utilized; ii) probe settings; and, iii) probe placement positions (process block 20). The computer system used may be, for example, a PC running on the Microsoft Windows operating system.

Figure 2:
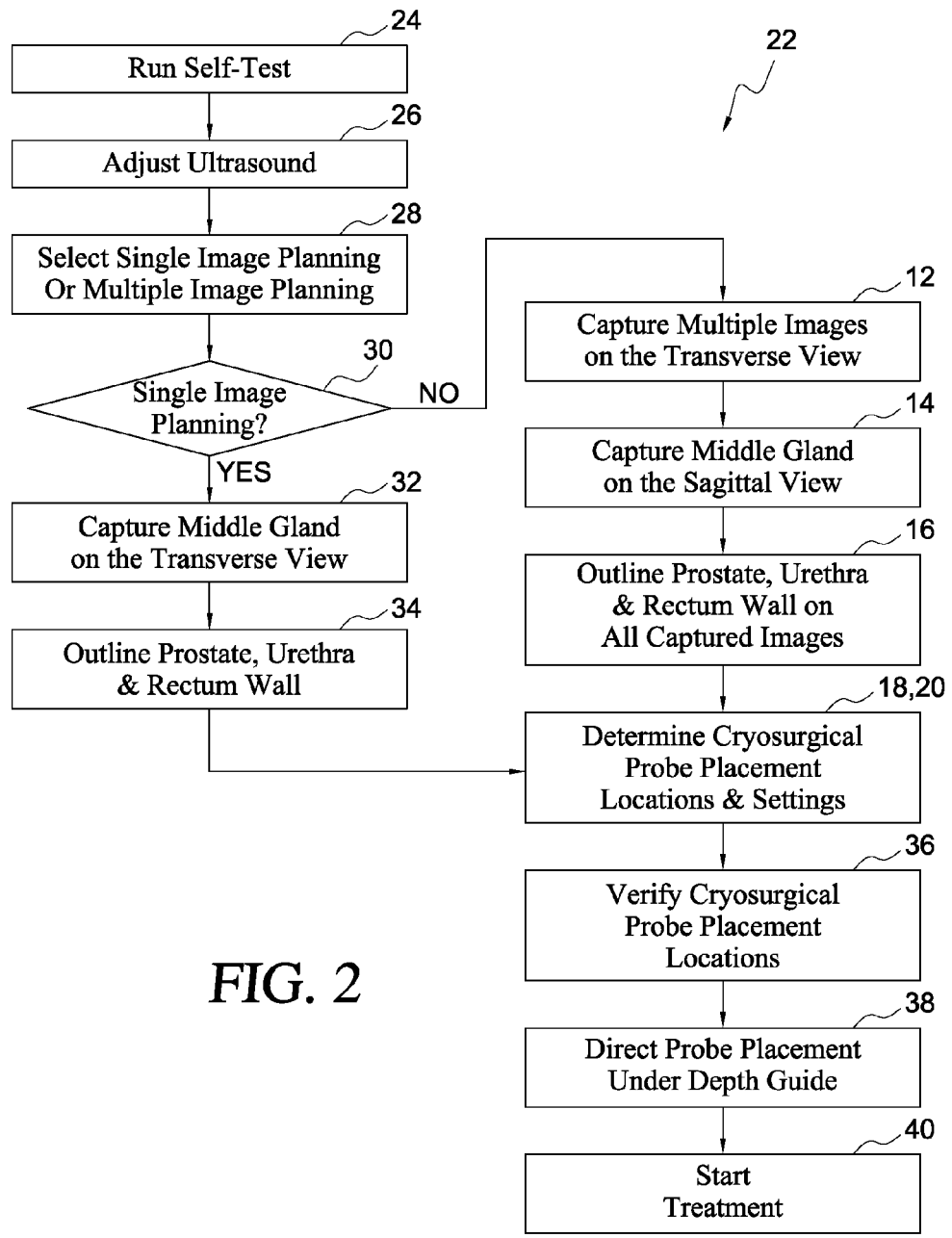
FIG. 2 is a more detailed flow chart of a preferred embodiment of the steps of the computer system.

Referring now to FIG. 2 a more detailed flow chart is presented, designated generally as 22, illustrating the steps provided by the computer system. Preliminary steps include running a pretest to assure system integrity (process block 24). A cryosurgical probe is dipped into sterilized liquid and then cryogenic fluid is passed through the cryosurgical probe. If the cryosurgical probe functions properly, no bubble should appear in the liquid and an iceball should form at the tip of the cryosurgical probe. A received ultrasound image is adjusted (process block 26) utilizing an ultrasound software system, as will be discussed in detail below. An option is then provided as to whether cryosurgical probe placement planning is to be provided using a single ultrasound image or multiple ultrasound images (process block 28).

If single image planning is selected (see decision block 30) the computer system confirms that single image planning has been selected and then captures the middle gland on the transverse view (process block 32). It then outlines the prostate, the urethra and the rectum wall on the transverse, middle gland view (process block 34).

If multiple image planning is selected (see decision block 30) the steps discussed with respect to FIG. 1 are applied. The computer system captures a plurality of transverse views of the prostate, as noted by numeral designation 12. It then captures a sagittal view of the prostate (process block 14). The capsule of the prostate, the urethra and the rectal wall of the patient are outlined with the assistance of the operator, utilizing the captured plurality of transverse views and the captured sagittal view (process block 16). A 3-dimensional model of the prostate, the urethra and the rectal wall is constructed utilizing the outlines noted above. The 3-dimensional model is used to determine i) the number of cryosurgical probes to be utilized; ii) probe settings; and, iii) probe placement positions. (See process blocks 18, 20.)

Cryosurgical probe placement locations are then verified (process block 36). A first criterion of verification is that each cryosurgical probe should be positioned at least 5 mm away from a periphery of a urethra. A second criterion of verification is that a cryosurgical probe should be positioned a safe margin away from a rectal wall. A third criterion of verification is that a distance between two cryosurgical probes that are next to each other should not exceed the sum of the radii of the lethal iceballs of the two cryosurgical probes. A fourth criterion of verification is that a distance from a cryosurgical probe to a periphery of a prostate should not exceed a radius of the lethal iceball of the cryosurgical probe. If all of these criteria are not simultaneously met, one or more of the least critical criteria may be compromised as desired to provide functionality.

Graphical depth guide software is utilized to direct probe placement under a depth guide (process block 38). This provides a graphical overlay on an ultrasound image of a sagittal view for assisting in the placement of cryosurgical probes. As will be discussed in detail below, the graphical overlay includes a scale and an icon of a cryosurgical probe. The icon is divided into two parts. The first part is colored in blue representing a length of the lethal ice of the variable cryosurgical probe. The second part is colored in while representing non-lethal ice of the variable cryosurgical probe. The distance from the graphical overlay to the surface of the ultrasound probe changes corresponding to the variable surgical probe selected. The lengths of the lethal ice and non-lethal ice change in a manner corresponding to a selected setting of the variable cryosurgical probe. The icon can be dragged and dropped horizontally along the scale. After determining the optimal location and the length of desired lethal ice by moving the depth guide, an operator can select a setting on a variable surgical probe accordingly then insert it into a patient along the graphical depth guide. Cryosurgical treatment is then commenced (process block 40).

Figure 3:
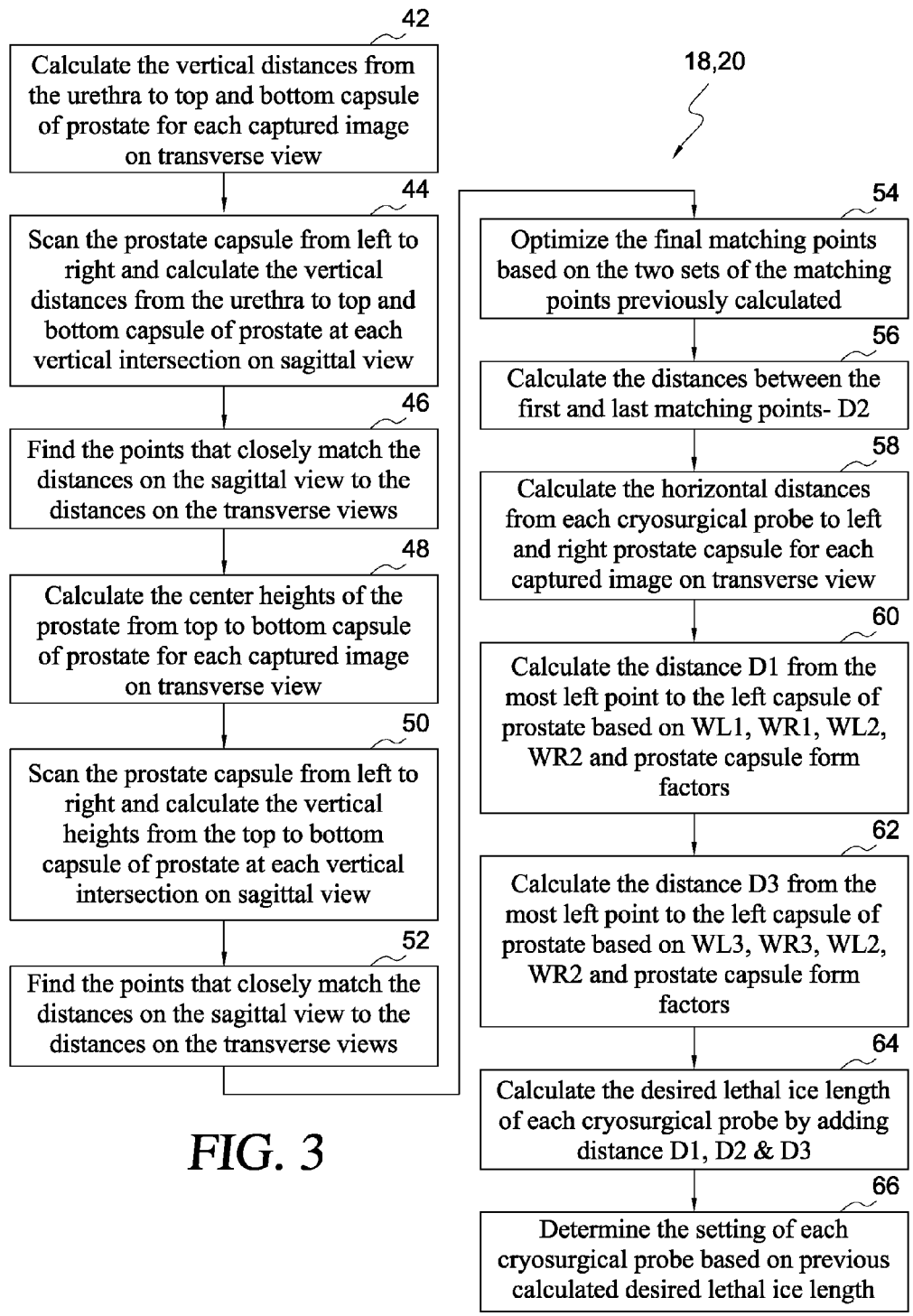
FIG. 3 is flow chart of the probe placement algorithm of FIG. 2.

Referring now to FIG. 3 the determination, by the computer system, of variable probe settings is illustrated, designated generally as 18, 20. This involves constructing the 3-dimensional model and utilizing the 3-dimensional model to determine i) the number of cryosurgical probes to be utilized; ii) probe settings; and, iii) probe placement positions.

Figure 4A:
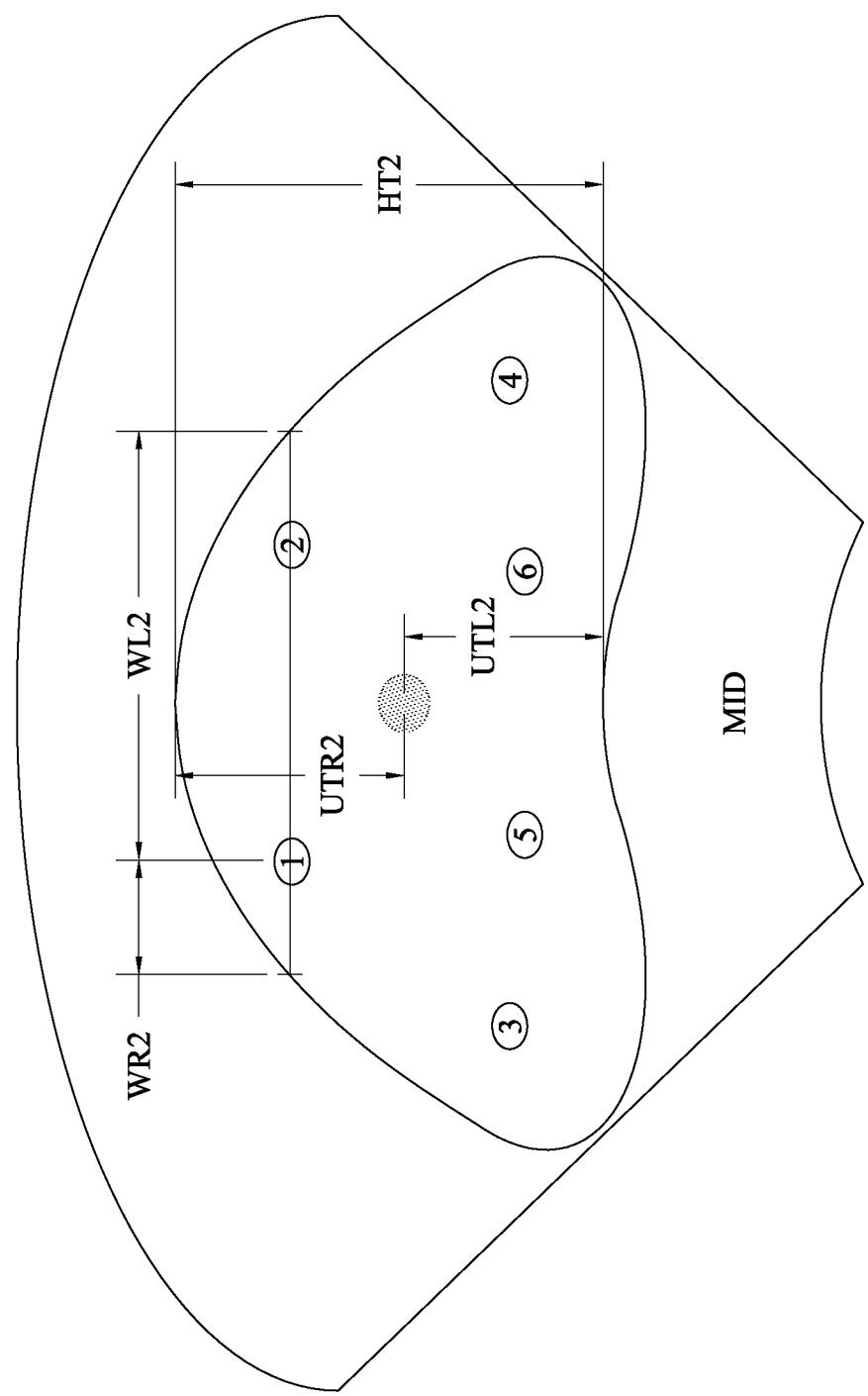
FIG. 4A is a schematic illustration of a transverse view of the prostate capsule showing parameters utilized by the computer system of the present invention, this transverse view being taken at a middle section of the prostate.
Figure 4B:
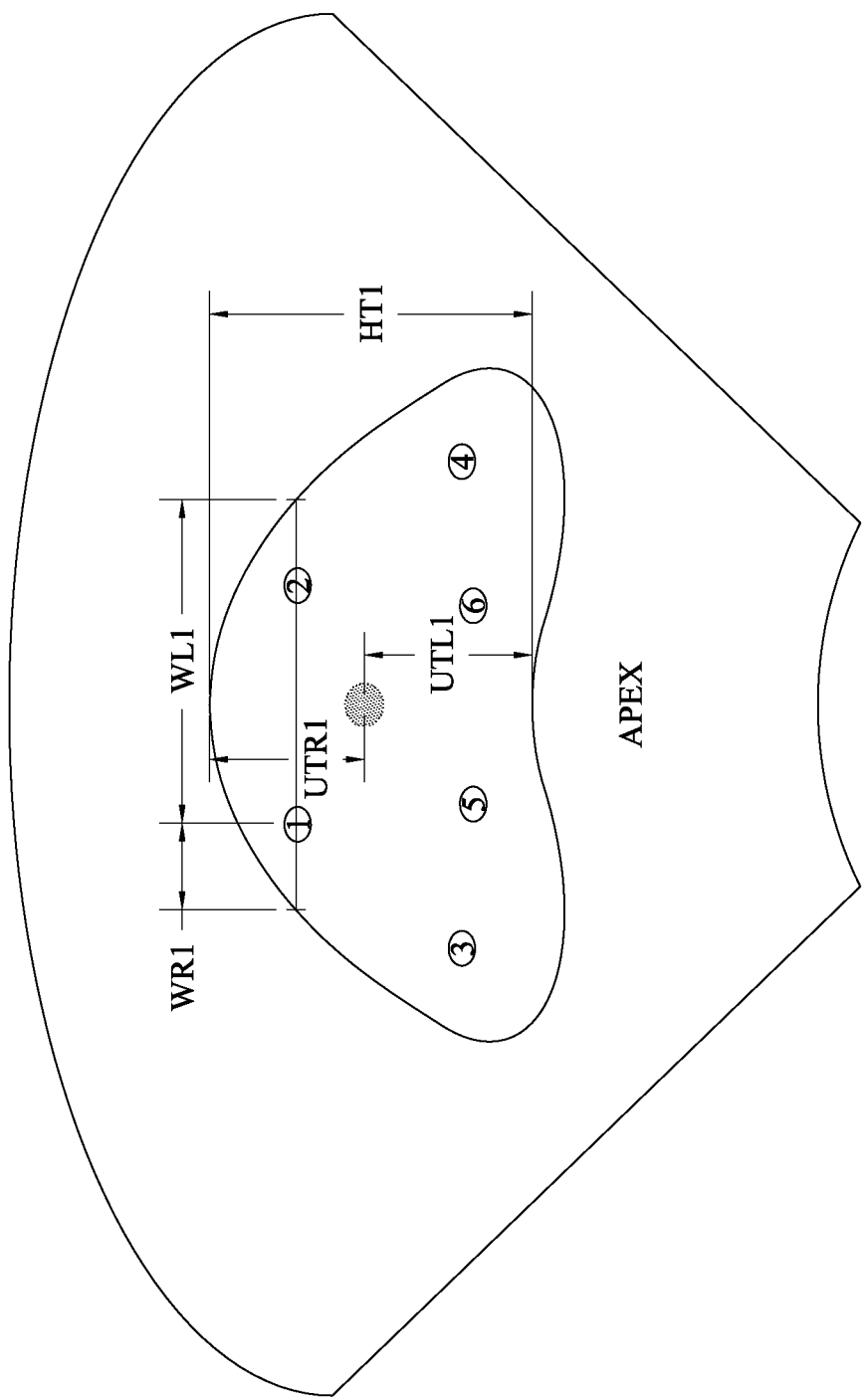
FIG. 4B is a schematic illustration of another transverse view of the prostate, this view being taken at the apex of the prostate.
Figure 4C:
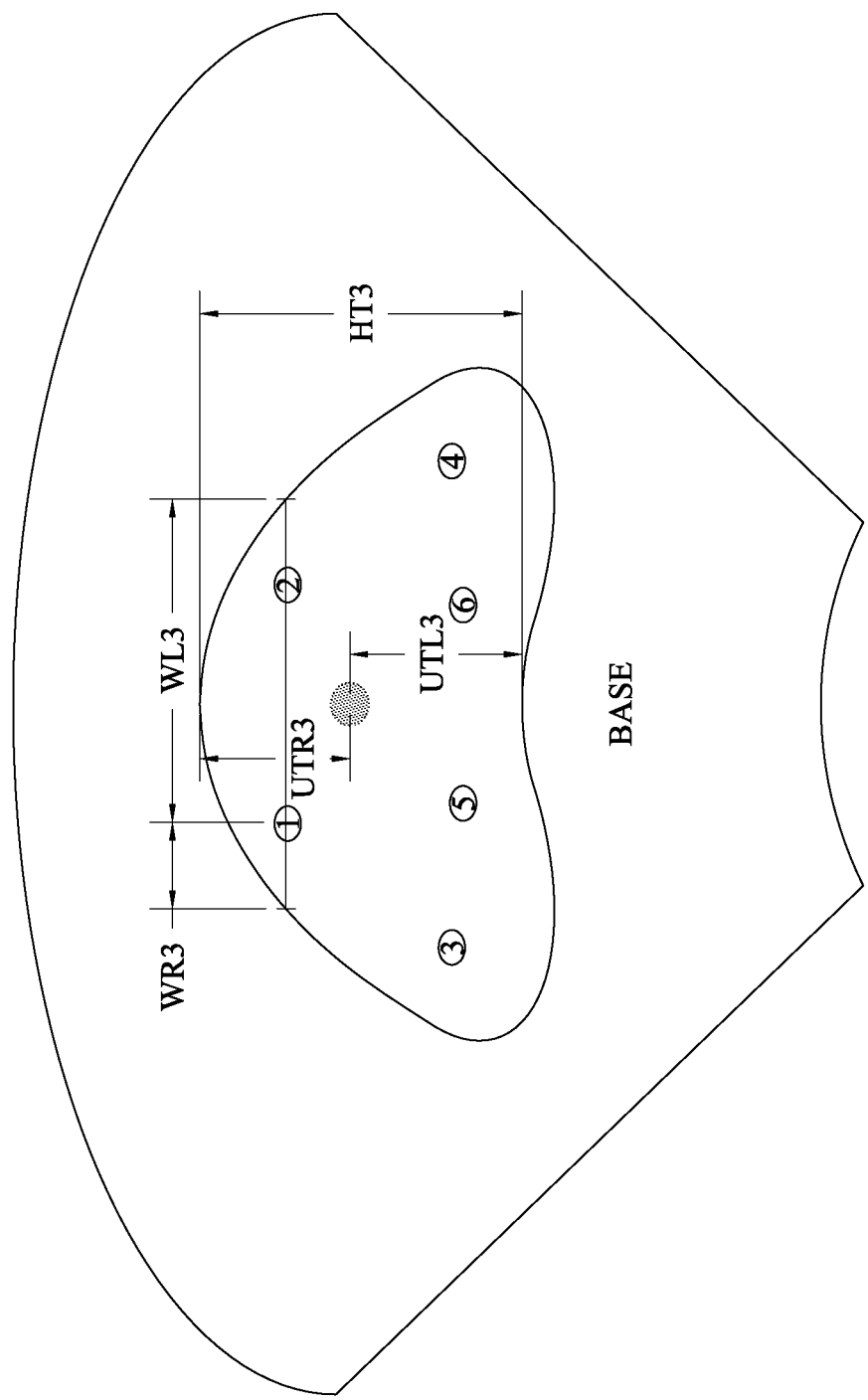
FIG. 4C is a schematic illustration of another transverse view of the prostate, this view being taken at the base of the prostate.

In a first step, vertical distances from the urethra to top and bottom capsules of the prostate are calculated for each captured transverse view (process block 42). Referring now to FIGS. 4A, 4B and 4C, transverse views of the prostate are shown along the largest (mid) section, the apex, and the base, respectively. At the apex, the vertical distance from the top of the capsule to the urethra is denoted as UTR1. At the largest section, the vertical distance from the top of the capsule to the urethra is denoted as UTR2. Similarly, at the base, the vertical distance from the top of the capsule to the urethra is denoted as UTR3. Although this example shows three sections captured, additional sections can be similarly captured and vertical distances (UTRn) calculated. Similar calculations of vertical distances from the urethra at the bottom of the prostate capsule are also provided as denoted UTL1, UTL2, UTL3.

Figure 5:
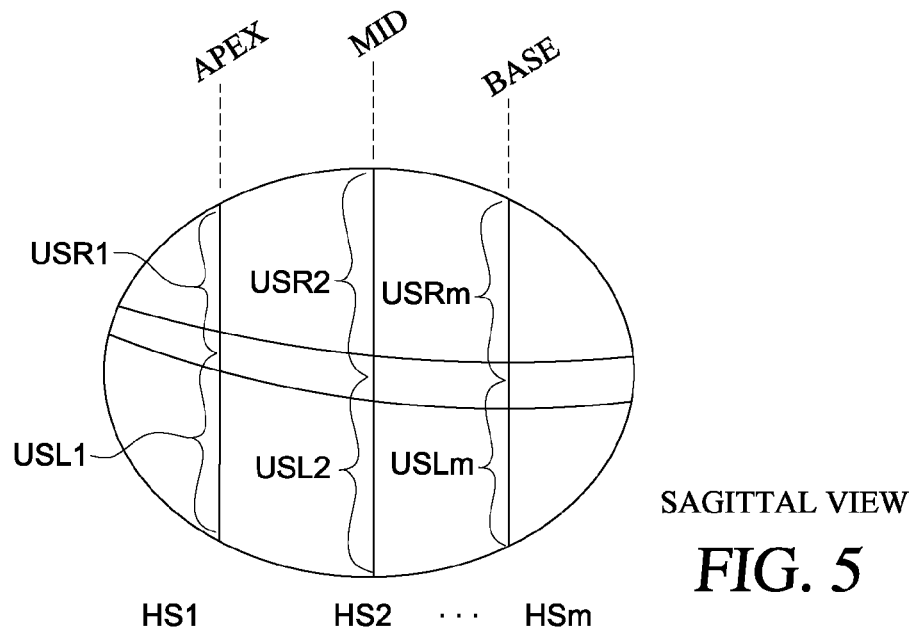
FIG. 5 is a schematic illustration of a sagittal view of the prostate taken at the center of the prostate.

The prostate capsule is then scanned on the sagittal view, from left to right, and the vertical distances from the urethra to the top and bottom capsule of the prostate at each vertical intersection on the sagittal view are calculated. As shown in FIG. 5 the sagittal view vertical distances are denoted as USR1, USR2, USR3 . . . USRm defining a USR list, and USL1, USL2, USL3 . . . USLm thus defining a USL list.

As can be seen in FIG. 3, process block 46, the software then finds the points that closely match the distances on the sagittal view to the distances on the transverse view. In other words, it finds a first of coordinates that closely match UTR1 from the USR list, UTL1 from the USL list, UTR2 from the USR list, UTL2 from the USL list, . . . UTRn from the USR list, UTLn from the USL list.

Next, as noted in process block 48, the software calculates the center heights of the prostate from the top to the bottom of the capsule of the prostate for each captured image on the transverse view, the transverse view center heights being denoted as HT1, HT2, HT3, . . . HTn. See also FIGS. 4A-4C.

As noted in process block 50, the prostate capsule is then scanned on the sagittal view and the vertical heights calculated from the top to the bottom of the capsule of the prostate, the sagittal view vertical heights being denoted as HS1, HS2, HS3, . . . HSm, defining an HS list. See also FIG. 5.

A second set coordinates that closely match HT1 from the HS list, HT2 from the HS list, . . . HTn from the HS list is then determined (process block 52). The software then utilizes the first set of coordinates and the second set of coordinates to calculate a final, optimized set of coordinates (process block 54).

The horizontal component, D2, of the distance between a first point of the optimized set of coordinates and a last point of the optimized set of coordinates, on the sagittal view, can then be calculated (process block 56).

Figure 6:
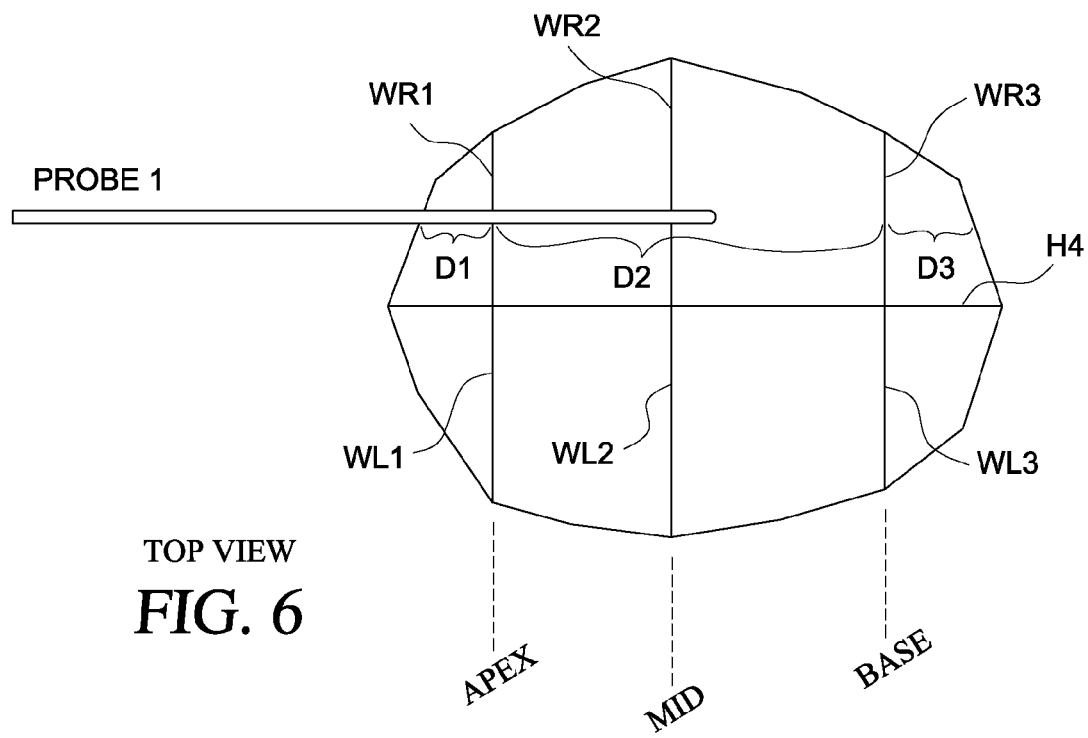
FIG. 6 is a schematic illustration of a top view of the prostate.

The horizontal components of the distances between each cryosurgical probe and the left of the prostate capsule are calculated for each transverse view, denoted as WR1, WR2, WR3, . . . WRn (process block 58). Similarly, the horizontal components of the distances between each cryosurgical probe and the right of the prostate capsule are calculated for each transverse view, denoted as WL1, WL2, WL3, . . . WLn. See also FIG. 6.

The software then utilizes selected WR1, WR2, WR3, . . . WRn; selected WL1, WL2, WL3, . . . WLn; and, D2 to calculate the distances, D1, from the first point of the optimized set of coordinates and the left of the prostate capsule, on the transverse view (process block 60).

Selected WR1, WR2, WR3, . . . WRn; selected WL1, WL2, WL3, . . . WLn; and, D2 are utilized to calculate the distances, D3, from the last point of the optimized set of coordinates and the right of the prostate capsule, on the transverse view (process block 62).

D1, D2 and D3 are then utilized to determine the length of a resultant lethal ice produced by the cryosurgical probes (process block 64). Appropriate settings of the cryosurgical probes based on the length of the resultant lethal ice can then be determined (process block 66).

Referring now to FIG. 7, implementation of the computer system into a cryosurgical system is illustrated, the cryosurgical system being designated generally as 70. The cryosurgical system 70 includes a cryosurgical probe system, designated generally as 72. The cryosurgical probe system 72 includes a plurality of cryosurgical probes 74; a control system 76 operatively connected to the plurality of cryosurgical probes 74; and, a cryogenic fluid source 78 operatively connectable to the control system 76. It also includes temperature probes 80.

A temperature data acquisition system 82 acquires the temperature of selected locations in the vicinity of the prostate utilizing the temperature probes 80, cryosurgical probes 74 and the control system 76.

An imaging system, preferably an ultrasound system 84, and most preferably an integrated ultrasound system is utilized for obtaining selected images of selected locations in the vicinity of the prostate.

A computer system, designated generally as 86, is operatively connected to the cryosurgical probe system 72 and the ultrasound system 84. The computer system 86 implements the steps outlined above with respect to FIGS. 1-6. It includes an integrated data processing system 88, suitable computer input/output devices such as a computer monitor, keyboard and mouse (collectively denoted as 90) and a video output 92. The video output 92 is provided so that an operator can conveniently view the display at another location away from the computer monitor itself. A video input 94 is provided from an external ultrasound system if an integrated ultrasound system is not utilized. The ultrasound system software should be capable of adjusting contrast, brightness, gains, focus, depth, and imaging size of the ultrasound image. Furthermore, the ultrasound system software should be capable of measuring a plurality of dimensions on an ultrasound image and of changing ultrasound views by toggling ultrasound transducers.

The fluid source may be, for example, a cryosurgical system such as that manufactured by present assignee, Endocare, Inc., Irvine, Calif. Such a cryosurgical system typically utilizes argon gas from an argon gas source to provide Joule-Thomson cooling of the cryosurgical probes. Alternatively, nitrogen can be used. Alternatively, a fluid supply system can be utilized that does not require an external fluid supply source. Heating of the cryosurgical probes is typically provided by a helium gas source for providing a helium gas flow through the nozzle of the cryosurgical probe. This provides a heating effect. Such heating of the cryosurgical probes is provided to unstick the probes from the treated tissue for cryoprobe removal. The cryosurgical probes may be of the type manufactured by present assignee, Endocare, Inc., Irvine, Calif.

A preferred cryosurgical probe is a variable cryosurgical probe such as that disclosed and claimed in co-owned U.S. patent Ser. No. 11/613,054 filed Dec. 19, 2006 to Duong, et al. entitled "Cryosurgical Probe With Vacuum Insulation Tube Assembly," incorporated herein by reference in its entirety. Ser. No. 11/613,054 is assigned to present assignee, Endocare, Inc., Irvine, Calif.

Another variable cryosurgical probe is disclosed and claimed in co-owned U.S. Pat. Publication US 20050192565 (U.S. patent Ser. No. 11/116,873), to Eum et al. entitled "Detachable Cryosurgical Probe with Breakaway Handle," incorporated herein by reference in its entirety. Ser. No. 11/116,873 is also assigned to present assignee, Endocare, Inc., Irvine, Calif.

Other cryosurgical probes are described in U.S. Pat. Publication No. 20040267248 (U.S. Ser. No. 10/603,883) to Duong, et al., entitled Detachable Cryosurgical Probe, filed on Jun. 25, 2003, incorporated herein by reference in its entirety; and, U.S. Pat. Publication US 20050010200 (U.S. patent Ser. No. 10/828,031), to Damasco, et al. entitled "Detachable Cryosurgical Probe," incorporated herein by reference in its entirety.

U.S. Pat. No. 6,643,535 issued to Damasco, et al. entitled "System for Providing Computer Guided Ablation of Tissue," is also incorporated herein by reference in its entirety.

A heat exchanger or cryostat is utilized to provide heat exchange between inlet gas and outlet gas. Although the heat exchanger is preferably a coiled fin tube heat exchanger various other types of heat exchangers may be utilized such as a tube-in-tube sintered cryostat, threaded cryostat, coiled/sintered cryostat, or stacked coil cryostat. These different types of cryostats are disclosed and claimed in U.S. Pat. Publication No. 20050010200 (U.S. Ser. No. 10/828,031), entitled Detachable Cryosurgical Probe, filed on Apr. 20, 2004, discussed above.

FIG. 8, is a screenshot of a computer display using present Assignee's Cryocare CS™ System, this screenshot being designated generally as 96. In this screen shot, the user has finished an outline 98 of the prostate and an outline 100 of the urethra, and he is performing an outline 102 of the rectal wall. The user can drag each dot 103 around so that the outline can fit the shape of the rectal wall. This corresponds to process block 16 of FIG. 1.

Referring now to FIG. 9, another screen shot is illustrated, designated generally as 104 showing use of a depth guide. The computer system is programmed with graphical depth guide software, as discussed above, capable of providing a graphical overlay on an ultrasound image 106 for assisting in the placement of the cryosurgical probes. This depth guide display format includes a first, (i.e. horizontal) scale 108 having a plurality of spaced markers. The cryosurgical probe icon 110 represents a cryosurgical probe. The cryosurgical probe icon 110 is positioned adjacent to the first scale 108. The cryosurgical probe icon defines a kill zone 112 (typically colored blue) and a non-lethal zone 114 of the cryosurgical probe. The kill zone 112 represents a lethal temperature range and the non-lethal zone represents a temperature above the lethal temperature range. The kill zone 112 and non-lethal zone 114 cooperate with the spaced markers 108 to provide a visual guide for placing the cryosurgical probes. These zones are dependent on variable settings of the probe.

A second (i.e. vertical) scale 116 orthogonal to the first scale 108 has a second plurality of spaced markers. The position of the cryosurgical probe icon 110 on the second scale 116 defines the distance of the cryosurgical probe 110 from an ultrasound probe, by referring to the image 106.

Thus, in a broad aspect, the present invention is a cryosurgical system for assisting an operator in placing and operating cryosurgical probes in the prostate of a human patient, wherein the cryosurgical probes are inserted through the skin of the perineal area of the patient and into the prostate. The cryosurgical system includes a treatment system, comprising a computer system which is programmed with software capable of optimizing the resultant ice produced by the cryosurgical probes for a specific patient. An ultrasound imaging system is integrated with the treatment system, wherein the computer software is programmed to adjust an ultrasound image.

Thus, while the preferred embodiments of the devices and methods have been described in reference to the environment in which they were developed, they are merely illustrative of the principles of the invention. For example, although ultrasound imaging has been described, certain applications may require guidance using various other imaging techniques such as CT guidance or MRI.

Other embodiments and configurations may be devised without departing from the spirit of the invention and the scope of the appended claims.

The invention claimed is:

1. A depth guide display format for a display system of a cryosurgical system, comprising:
    a. a first scale having a plurality of spaced markers; and,
    b. a cryosurgical probe icon representing a cryosurgical probe, the cryosurgical probe icon being positioned adjacent to the first scale, the cryosurgical probe icon defining a kill zone and a non-lethal zone of the cryosurgical probe, the kill zone representing a lethal temperature range and the non-lethal zone representing a temperature above the lethal temperature range, wherein the kill zone and non-lethal zone in combination with the spaced markers provide a visual guide for placing at least one cryosurgical probe, the kill zone and non-lethal zone being dependent on variable settings of the cryosurgical probe.

2. The depth guide display format of claim 1, further comprising a second scale orthogonal to the first scale, the second scale having a second plurality of spaced markers, wherein a position of the cryosurgical probe icon on the second scale defines a distance of the cryosurgical probe from an ultrasound probe.

3. The depth guide display format of claim 1, wherein the kill zone is represented by a blue color.

4. The depth guide display format of claim 1, wherein the cryosurgical probe icon is capable of being dragged and dropped horizontally along the first scale for determining an optimal location and length of desired lethal ice.

5. The depth guide display format of claim 1, wherein (i) the cryosurgical probe icon represents a variable cryosurgical probe, and (ii) the kill zone and the non-lethal zone are dependent on variable settings of the variable cryosurgical probe.

6. The depth guide display format of claim 1, wherein (i) the cryosurgical probe icon represents a variable cryosurgical probe, and (ii) the cryosurgical probe icon is capable of being dragged and dropped horizontally along the first scale for determining an optimal location and length of desired lethal ice.

7. The depth guide display format of claim 6, wherein an operator accordingly selects a setting on the variable cryosurgical probe then inserts it into a patient along the graphical depth guide.

8. The depth guide display format of claim 1, wherein the cryosurgical probe icon represents a cryosurgical probe for use in the prostate of a human patient.

9. Graphical depth guide software capable of providing a graphical overlay on an ultrasound image for assisting in the placement of at least one cryosurgical probe, the software implementing the steps, comprising:
    a. displaying a first scale having a plurality of spaced markers; and
    b. displaying a cryosurgical probe icon representing a cryosurgical probe, the cryosurgical probe icon being positioned adjacent to the first scale, the cryosurgical probe icon defining a kill zone and a non-lethal zone of the cryosurgical probe, the kill zone representing a lethal temperature range and the non-lethal zone representing a temperature above the lethal temperature range, wherein the kill zone and non-lethal zone in combination with the spaced markers provide a visual guide for placing the cryosurgical probe, the kill zone and non-lethal zone being dependent on variable settings of the cryosurgical probe.

10. The graphical depth guide software of claim 9, wherein the software further implements the step of displaying a second scale orthogonal to the first scale, the second scale having a second plurality of spaced markers, and wherein the position of the cryosurgical probe icon on the second scale defines a distance of the cryosurgical probe from an ultrasound probe.

11. The graphical depth guide software of claim 9, wherein the kill zone is represented by a blue color.

12. The graphical depth guide software of claim 9, wherein the cryosurgical probe icon is capable of being dragged and dropped horizontally along the first scale for determining an optimal location and length of desired lethal ice.

13. The graphical depth guide software of claim 9, wherein the cryosurgical probe icon represents a variable cryosurgical probe, and wherein the kill zone and the non-lethal zone are dependent on adjustable settings of the variable cryosurgical probe.

14. The graphical depth guide software of claim 9, wherein (i) the cryosurgical probe icon represents a variable cryosurgical probe, and (ii) the cryosurgical probe icon is capable of being dragged and dropped horizontally along the first scale for determining an optimal location and length of desired lethal ice.

15. The graphical depth guide software of claim 9, wherein the cryosurgical probe icon represents a cryosurgical probe for use in the prostate of a human patient.

* * * * *